United States Patent [19]

Barcza

[11] 4,132,725

[45] Jan. 2, 1979

[54] SUBSTITUTED 3,1-BENZAZASILIN-4-ONES

[75] Inventor: Sandor Barcza, West Orange, N.J.

[73] Assignee: Sandoz, Inc., East Hanover, N.J.

[21] Appl. No.: 881,686

[22] Filed: Feb. 27, 1978

[51] Int. Cl.² ............................................. C07F 7/10
[52] U.S. Cl. ........................... 260/448.2 N; 424/184
[58] Field of Search ................................. 260/448.2 N

[56] References Cited

U.S. PATENT DOCUMENTS

| 3,065,251 | 11/1962 | Jones et al. | 260/448.2 N |
| 3,103,529 | 9/1963 | Tamborski et al. | 260/448.2 N |
| 3,120,565 | 2/1964 | Kollonitsch | 260/448.2 N X |
| 3,131,203 | 4/1964 | Erickson et al. | 260/448.2 N |
| 3,143,560 | 8/1964 | Wasserman et al. | 260/448.2 N |
| 3,159,661 | 12/1964 | Jones et al. | 260/448.2 N |

*Primary Examiner*—Paul F. Shaver
*Attorney, Agent, or Firm*—Gerald D. Sharkin; Robert S. Honor

[57] ABSTRACT

Benzazasilin-4-ones of the formula

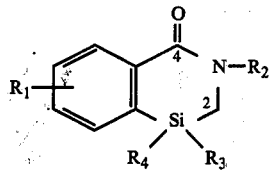

where
$R_1$ represents H or alkyl of 1-5 carbon atoms,
$R_2$ represents alkyl of 1-5 carbon atoms,
$R_3$ represents alkyl of 1-5 carbon atoms or

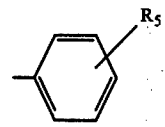

where
$R_5$ represents H, alkyl of 1-5 carbon atoms, halo having an atomic weight of about 19-36, alkoxy having 1-5 carbon atoms, or

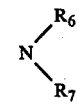

where $R_6$ and $R_7$ each, independently, represent alkyl having 1-2 carbon atoms, and
$R_4$ represents alkyl having 1-3 carbon atoms, e.g., 1-(p-chlorophenyl)-2,3-dihydro-1,3-dimethyl-3,1-benzazasilin-4(1H)-one, are prepared from the appropriate lithiated N-alkyl benzamide and a halomethyl halosilane and are useful as antiobesity agents or sleep inducers.

3 Claims, No Drawings

SUBSTITUTED 3,1-BENZAZASILIN-4-ONES

This invention relates to 1,1-disubstituted-3,1-benzazasilin-4-ones of the formula

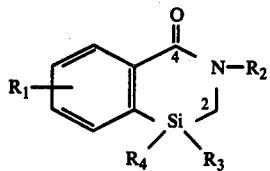 (I)

where
R₁ represents H or alkyl of 1-5 carbon atoms,
R₂ represents alkyl of 1-5 carbon atoms,
R₃ represents alkyl of 1-5 carbon atoms or

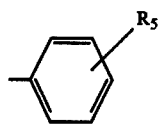

where
R₅ represents H, alkyl of 1-5 carbon atoms, halo having an atomic weight of about 19-36, alkoxy having 1-5 carbon atoms, or

where R₆ and R₇ each, independently, represent alkyl having 1-2 carbon atoms, and
R₄ represents alkyl having 1-3 carbon atoms.

When the substituents on the compounds I above are alkyl having 3 or more carbon atoms, they may be straight chain or branched. The alkyl substituents possibly having 1-5 carbon atoms preferably contain 1-3 carbon atoms and more preferably represent methyl or ethyl, whereas when the alkyl substituents are said to contain 3 or less carbon atoms, they preferably represent methyl. When the substituent R₅ represents said alkoxy, it may be straight chain or branched, preferably contains 1-3 carbon atoms and more preferably represents methoxy or ethoxy. Said halo represents more specifically chloro and fluoro.

The compounds I are prepared in a two-step procedure. The first step involves lithiating amides of the formula

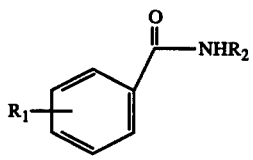 (II)

where R₁ and R₂ are as defined above, with a compound of the formula

R₈Li   (III)

where
R₈ represents alkyl of 1-4 carbon atoms, such as methyl, ethyl, isopropyl and the like, in inert atmosphere, such as nitrogen gas, and inert solvent such as hydrocarbon, for example, hexane or heptane, or an ether, e.g., diethyl ether or tetrahydrofuran, at a temperature of about −50° C. to +50° C., preferably about −40° C. to 0° C. for about 0.5 to about 48 hours. The second step comprises treating the lithiated derivative of the compound of formula II with a compound of the formula

 (IV)

where each Y, independently, represents halo, preferably chloro or bromo, and R₃ and R₄ are as defined above, at a temperature of about −80° C. and about −50° C. for about 0.5 to 48 hours. Solvents such as hydrocarbons or ethers may be utilized in the second step if desired. The resulting product I may then be separated using standard techniques including chromatography and distillation.

In none of the processes described above is the particular solvent or temperature of reaction critical, and variation in accordance with the knowledge and techniques of the ordinary art-skilled chemist provides the products indicated.

To the extent not specifically indicated herein, it should be understood that the starting materials described are either known or may be prepared from known materials by methods analogous to processes described in the literature.

The compounds of formula I are useful because they possess pharmacological activity in animals. In particular, the compounds wherein R₃ represents the indicated phenyl or substituted phenyl moiety are useful as sleep inducers as indicated in standard tests, such as the 30 word adjective test basically as described by Irwin, S. (Gordon Research Conference, Medicinal Chemistry, 1959), and Chen (Symposium on Sedative and Hypnotic Drugs, Williams and Wilkins, 1954) wherein the mice involved are administered 50-200 mg/kg of animal body weight of test compound I.P., and also as indicated in the test on mice regarding hexobarbitol interaction, wherein anesthesia is induced by intravenous injection of 70 mg/kg of hexobarbital. Immediately after recovery, the test animals are administered test compound I.P., and reinduction of anesthesia results with compound having the indicated C.N.S. depressant effect. This method is a modification of that described by Winter et al. (J. Pharmacol. Exp. Therap. 94: 7-11, 1948).

The compounds of formula I wherein R₃ represents said alkyl moiety are useful as antiobesity agents as indicated in a glucose transport test in which male Wistar rats are dosed orally with test compound after at least 20 hrs. of fasting. One hour after receiving the drug the animal is sacrificed and the upper small intestine is removed and washed with glucose-saline. A 5 cm. section of the intestine is everted, and one end is tied to form a sac. The sac is filled with oxygen saturated Kreb's bicarbonate buffer. The other end of the sac is then closed and the sac is incubated in 10 ml. of oxygen saturated bicarbonate buffer for 60 minutes at 37° C. Initially, the inside and outside solutions contain 0.3% of glucose. At the end of the incubation time, the glucose content of the inner and outer solutions is determined using the standard Autoanalyzer procedure. The inhibition of glucose transport is then compared to controls.

For these uses, the compounds of formula I may be combined with a pharmaceutically acceptable carrier or adjuvant, and may be administered orally in such forms as tablets, capsules, elixirs, suspensions and the like, or parenterally in the form of a sterile injectable solution or suspension. The dosage will vary depending on the compound employed and the mode of administration and treatment desired. However, in general, satisfactory results are obtained when a compound of formula I is administered at a daily dosage of from about 50 mg. to about 200 mg. per kilogram of animal body weight, conveniently given in divided doses 2 to 4 times a day or in sustained release form. For the larger mammals, the total daily dose is in the range of from about 250 mg. to 1000 mg., and dosage forms, conveniently oral dose forms, suitable for internal use comprise from about 60 mg. to about 500 mg. of the active compound in intimate admixture with a solid or liquid pharmaceutically acceptable carrier or diluent.

Capsules containing 200 mg. of active ingredient and 200 mg. lactose may be prepared by conventional techniques and are useful in inducing sleep or as an anti-obesity agent at a dose of one capsule 2 to 4 times a day.

EXAMPLE 1

1-(p-Chlorophenyl)-2,3-Dihydro-1,3-Dimethyl-3,1-Benzazasilin-4(1H)-one

To 11.3 g. (83.7 m mol) of N-methyl benzamide in 200 ml. of absolute tetrahydrofuran under nitrogen is added 115 ml. (2.22 × 87.7 m mol) of 1.6 N n-butylithium solution in hexane at from −40° C. to 0° C. with stirring. The reaction mixture contains a semi-solid and is stirred at 25° C. for 45 min., re-cooled using a dry ice-acetone bath and 20.5 g. (85.7 m mol) of chloromethyl-p-chlorophenyl-methyl chlorosilane is added between −78° C. and −55° C. The mixture is allowed to warm up to room temperature over a few hours and is stirred until 16 hours have passed. The mixture is then poured onto ice and toluene and the resulting organic layer is washed three times with water, dried with sodium sulfate and concentrated in vacuo at 40° C. to a thick oil. This oil is chromatographed on silica gel by eluting with hexane:chloroform (2:3) to obtain a thick oil which appears essentially as a single spot after thin layer chromatography. A portion is then purified by evaporative distillation to provide the product; b.p. 153°–157° C. at 0.03 mm Hg.

When the above process is carried out and in place of N-methyl benzamide there is used
  (i) N-methyl p-toluamide, there is obtained
  (i) 1-(p-chlorophenyl)-2,3-dihydro-1,3,7-trimethyl-3,1-benzazasilin-4(1H)-one.

When the above detailed process is carried out and in place of chloromethyl-p-chlorophenyl methyl chlorosilane there is used
  (ii) chloromethyl methyl-o-tolyl chlorosilane,
  (iii) chloromethyl methyl-p-methoxyphenyl chlorosilane, or
  (iv) chloromethyl p-dimethylaminophenyl-methyl chlorosiline, there is obtained
  (ii) 1-(o-tolyl)-2,3-dihydro-1,3-dimethyl-3,1-benzazasilin-4(1H)-one,
  (iii) 2,3-dihydro-1,3-dimethyl-1-(p-methoxyphenyl)-3,1-benzazasilin-4(1H)-one, or
  (iv) 2,3-dihydro-1,3-dimethyl-1-(p-dimethylaminophenyl)-3,1-benzazasilin-4(1H)-one, respectively.

EXAMPLE 2

2,3-Dihydro-1,1,3-Trimethyl-3,1-Benzazasilin-4(1H)-one

Under nitrogen 448 ml. (2.2 × 0.325 mol) of 1.6 M of n-butyl lithium solution in hexane is added to 44 g. (0.325 mol) of N-methylbenzamide dissolved in 570 ml. of absolute tetrahydrofuran at between −78° and −40° C. with stirring. Some semi-solid formation occurs at the lower temperature range but the mixture is readily stirred at −40° C. The mixture is stirred for one hour at 25°–30° C., cooled in a dry ice bath and 46.6 g. (0.325 mol) of chloromethyl dimethyl chlorosilane is added at −78° to −40° C. The mixture warms to about 20° C. in about three hours and stirring is continued overnight.

The contents are then poured onto ice plus toluene, the resulting organic phase is washed with water, dried with sodium sulfate and concentrated in vacuo to provide crude product as an oil. The oil is fractionated at 0.02 mm Hg. pressure through a column packed with stainless steel. The fractions boiling between 80° and 110° C. contain product and some N-methylbenzamide as determined by gas-liquid chromatography. These fractions are combined, dissolved in about 30 ml. of toluene and 120 ml. of cyclohexane and washed ten times with 30 ml. of methanol, mixed with 120 ml. of water and washed once again with 100 ml. of water. The organic phase is dried with sodium sulfate and concentrated in vacuo to provide product which, when distilled to obtain a pure sample, displayed a b.p. of 99°–103° C. at 0.06–0.025 mm Hg.

What is claimed is:
1. A compound of the formula

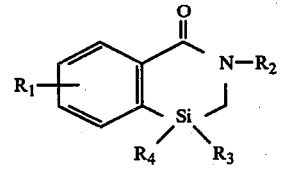

where
  $R_1$ represents H or alkyl of 1–5 carbon atoms,
  $R_2$ represents alkyl of 1–5 carbon atoms,
  $R_3$ represents alkyl of 1–5 carbon atoms or

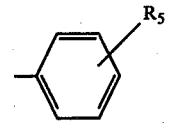

where
  $R_5$ represents H, alkyl of 1–5 carbon atoms, halo having an atomic weight of about 19–36, alkoxy having 1–5 carbon atoms, or

where
  $R_6$ and $R_7$ each independently, represent alkyl having 1–2 carbon atoms, and
  $R_4$ represents alkyl having 1–3 carbon atoms.
2. The compound of claim 1 which is 1-(p-chlorophenyl)-2,3-dihydro-1,3-dimethyl-3,1-benzazasilin-4(1H)-one.
3. The compound of claim 1 which is 2,3-dihydro-1,1,3-trimethyl-3,1-benzazasilin-4(1H)-one.

* * * * *